US008207070B2

(12) United States Patent
Li et al.

(10) Patent No.: US 8,207,070 B2
(45) Date of Patent: *Jun. 26, 2012

(54) WETTABLE POLYOLEFIN FIBERS AND FABRICS

(75) Inventors: Sheng-Shing Li, Danbury, CT (US); Andrew J. Leggio, Franklin Sqaure, NY (US); George H. Menzie, Sandy Hook, CT (US); David Devore, Nyack, NY (US); John J. McNamara, Putnam Valley, NY (US); TaHau Yu, Nanuet, NY (US); Douglas W. Horsey, Briarcliff Manor, NY (US)

(73) Assignee: Techmer PM, LLC, Rancho Dominguez, CA (US)

( * ) Notice: Subject to any disclaimer, the term of this patent is extended or adjusted under 35 U.S.C. 154(b) by 1008 days.

This patent is subject to a terminal disclaimer.

(21) Appl. No.: 10/045,391

(22) Filed: Nov. 9, 2001

(65) Prior Publication Data

US 2002/0169429 A1 Nov. 14, 2002

Related U.S. Application Data

(60) Provisional application No. 60/252,573, filed on Nov. 22, 2000, provisional application No. 60/274,161, filed on Mar. 8, 2001, provisional application No. 60/311,287, filed on Aug. 9, 2001, provisional application No. 60/322,638, filed on Sep. 17, 2001.

(51) Int. Cl.
*B32B 27/32* (2006.01)

(52) U.S. Cl. .......... 442/118; 428/364; 428/373; 442/60; 442/97; 442/102; 442/110; 510/356; 510/438; 524/376; 524/379; 524/381; 524/385; 604/370; 604/372

(58) Field of Classification Search .......... 428/364, 428/373; 604/370, 372; 510/356, 438; 442/97, 442/102, 60, 110, 118; 524/376, 379, 381, 524/385

See application file for complete search history.

(56) References Cited

U.S. PATENT DOCUMENTS

| 3,048,266 A | 8/1962 | Hackhel et al. ............ 206/45.34 |
| 4,304,234 A | 12/1981 | Hartmann ...................... 128/287 |
| 5,001,015 A | 3/1991 | Havens .......................... 428/516 |
| 5,240,985 A | 8/1993 | Gardiner ........................ 524/274 |
| 5,262,233 A | 11/1993 | Sudo et al. .................... 428/327 |
| 5,272,196 A | 12/1993 | Gardiner ........................ 524/252 |
| 5,281,438 A | 1/1994 | Gardiner et al. ............. 427/256 |
| 5,328,951 A | 7/1994 | Gardiner ........................ 524/287 |
| 5,348,736 A * | 9/1994 | Patel et al. ................... 424/70.9 |
| 5,464,691 A | 11/1995 | Gardiner et al. ............. 428/336 |
| 5,614,574 A | 3/1997 | Sheth ............................. 524/140 |
| 5,654,086 A | 8/1997 | Nishijima et al. ............ 442/199 |
| 5,669,798 A | 9/1997 | Koczab ......................... 442/362 |
| 5,698,322 A | 12/1997 | Tsai et al. ...................... 428/373 |
| 5,733,822 A * | 3/1998 | Gessner et al. ................. 442/35 |
| 5,804,625 A | 9/1998 | Temperante et al. ......... 524/188 |
| 6,070,107 A * | 5/2000 | Lombardi et al. ............. 700/119 |
| 6,146,757 A * | 11/2000 | Mor et al. ...................... 428/364 |
| 6,153,701 A | 11/2000 | Potnis et al. .................. 525/191 |
| 6,218,009 B1 * | 4/2001 | Tsai et al. ...................... 428/373 |
| 6,239,047 B1 | 5/2001 | Erdos et al. ................... 442/119 |
| 6,784,235 B2 * | 8/2004 | Gupta et al. ................... 524/376 |

FOREIGN PATENT DOCUMENTS

| DE | 2109030 | 9/1972 |
| EP | 547846 A1 * | 6/1993 |
| EP | 0800833 | 10/1997 |
| EP | 0888786 | 1/1999 |
| EP | 0 931 805 | 7/1999 |
| EP | 1152027 | 11/2001 |
| WO | 00/22061 | 4/2000 |
| WO | 00/28143 | 5/2000 |
| WO | 01/14621 | 3/2001 |

OTHER PUBLICATIONS

"Unilin Alcohols," Technical Release, Petrolite Specialty Polymers Group (1985).*
Derwent Abstract 61211T-AF for DE 2109030 (1972).
D. Bergbreiter et al., Macromolecules, (1992), vol. 25. pp. 636-643.
Atmer. Antifog Agent for Agricultural and Food-Packaging Films. Polymer Additives Group, Ciba Specialty Chemicals Corp.
Unithox® Ethoxylated Alcohols. Technical Release 4022.0. (1996). Petrolite Corp., Polymers Division.

* cited by examiner

*Primary Examiner* — Peter Y Choi
(74) *Attorney, Agent, or Firm* — Brooks Kushman P.C.

(57) ABSTRACT

Polyolefin woven and nonwoven fibers, filaments and fabrics made therefrom which comprise a melt blend which comprises
(a) a polyolefin; and
(b) at least one compound of the formula (I)

$$R_1\text{—(hydrophilic oligomer)} \qquad (I)$$

wherein
$R_1$ is a straight or branched chain alkyl of 22 to 40 carbon atoms and the hydrophilic oligomer is a homo- or co-oligomer consisting of monomer units derived from monomers selected from the group consisting of ethylene oxide, propylene oxide, ethylene glycol, propylene glycol, epichlorhydrin, acrylic acid, methacrylic acid, ethylene imine, caprolactone, vinyl alcohol and vinyl acetate;
and wherein the hydrophilic oligomer consists of between 2 and 10 monomer units, exhibit excellent durable wettability. The fabrics are useful in disposable diapers, training pants, feminine napkins, tampons, incontinence care products, wet and dry wipes, wound dressings, surgical capes, filter medial, battery separators and the like.

12 Claims, No Drawings

WETTABLE POLYOLEFIN FIBERS AND FABRICS

This application claims the benefit under 35 USC 119(e) of U.S. Provisional application Nos. 60/252,573, filed Nov. 22, 2000; 60/274,161, filed Mar. 8, 2001; 60/311,287, filed Aug. 9, 2001; and 60/322,638, filed Sep. 17, 2001.

The present invention relates to novel olefin polymer woven or nonwoven fibers that exhibit durable wettability. The fibers are especially useful in sanitary articles such as diapers, feminine hygiene products and incontinence care products.

BACKGROUND

Polyolefins, especially polypropylene, are used in large quantities to make woven and nonwoven fabrics. Polyolefin nonwoven fabrics, such as carded webs, spunbond, melt-blown or composites thereof, are preferred as components in sanitary articles such as single use diapers, feminine hygiene products and incontinence care products. The recognized benefits of polyolefin based, especially polypropylene, fabrics include the relatively low raw material cost, ease of manufacturing, desirable strength to basis weight ratio and softness.

Sanitary articles generally contain an absorbent core component of materials capable of absorbing several times their weight in liquids. Usually the article includes at least one outer covering or lining which contacts the user's skin on one side of the core and an exterior layer contacting the environment on the other side of the core. Softness and liquid permeability are required of fabrics used for the inner linings. The liquid permeability should take the form of allowing liquid to pass through the fabric and into the inner absorbent core, while not actually absorbing fluids in the process. An additional desired feature is for the inner lining, i.e., the cover sheet for the absorbent core, to remain fluid permeable even after extended wear and repeated insults of fluid, such as routinely occurs with infant diapers in situ. Another highly desired, but difficult to provide, feature of inner lining fabrics is that they resist having liquids collected in the absorbent core bleed back through to the user's skin when pressure is applied, such as an infant sitting in a wet diaper.

Nonwoven fabrics and composites made of cellulosic materials pass and absorb liquids even after repeated insults, but they do not routinely resist the flow back of the retained fluids under pressure. Thermoplastic fibers, such as polyesters and polyolefins have already been described as being preferred for these end uses for economic, aesthetic and strength reasons. However, polypropylene is, by its nature, hydrophobic. When spun into fibers or filaments which are used to form a fabric, the resulting fabric is also hydrophobic or non-wettable. Thus, the fabric must be specially treated or altered in some way to render the fabric wettable, that is, able to allow the passage or transfer of fluids, if the fabric is to be suitable for use as an inner lining fabric for a sanitary article.

For purposes of clarification, it should be noted that absorption indicates that the material actually swells with added water. In contrast, wettability, as defined herein, denotes a change in surface tension that permits a layer of water to form on the surface of a solid, such as a fiber, for the purpose of facilitating the movement of the liquid flow past or through the wettable material.

It is known in the industry that certain surfactants, such as TRITON X-100 from Rohm and Haas, can be applied as an aqueous solution or suspension to the surface of hydrophobic fibers, filaments or nonwoven fabrics with the resulting effect of rendering the fibers, filaments or fabrics wettable, although not absorbent. These topical treatments can be applied by any means familiar to one skilled in the art, such as foaming spraying, dip-and squeeze or gravure roll. In almost every case, some sort of heating step is required to remove residual water or solvent used to prepare the surfactant solution or suspension. This step adds significantly to the manufacturing costs and complexity. Further, thermoplastics are altered by exposure to heat and careful monitoring of the heating process is required to ensure that fabric properties are not adversely affected. Further, the surfactants are not strongly chemically bonded to the fiber or filament surfaces, such topical treatments are not durable. They tend to wash off during repeated fluid insults or rub off during use.

In an effort to correct this deficiency, corona discharge treatments have been used to alter the electrochemical potential of the surfaces of fibers or filaments. The effect is to render surfaces more reactive with the result that hydrophobic surfaces become more wettable. However, these electrical potential changes are also not permanent, being particularly subject to environmental effects, such as storage in moist environments.

An additional advancement is the use of surface chemical treatments where the surfactants are covalently bonded to the polymer.

Another approach is the incorporation of chemical agents in the thermoplastic polymer before it is extruded into fibers, filaments or nonwoven fabrics. Agents, such as siloxanes, have been proposed for this purpose. Here, the object is to impart a durable change in the wettability of the fibers or filaments. The performance model theory states that the melt additives become dispersed in the molten polymer and are bound in the matrix when the polymer cools during fiber or filament quenching. Over time, due to the effects of further processing, the additive rises to the surface of the fibers or filaments, a phenomenon called blooming, imparting durable wettabilty.

Bergbreiter and Srinivas in *Macromolecules* 25 (1992), 636-643, disclose an "entrapment functionalization" approach towards modifying the surface of high-density polyethylene. Block cooligomers of polyethylene and poly (ethylene glycol) are prepared and intimately mixed with virgin polyethylene. Analysis of polymer films prepared from this mixture showed that the poly(ethylene glycol) units ended up primarily at the outermost layers of the film.

U.S. Pat. No. 5,464,691 discloses the use of an tri-block amphiphilic resin towards modifying the surface energy of a polyolefin film. The amphiphilic resins are composed of two hydrocarbon sections and a polar section. The hydrocarbon sections are derived from, for example, long-chain aliphatic carboxylic acids, aliphatic alcohols, and the like, and the polar section is derived from a telechelic diol, for example polyethylene glycol.

U.S. Pat. Nos. 5,240,985, 5,272,196, 5,281,438, 5,328,951 disclose the use of an amphiphile towards increasing the surface energy of polyolefins. The amphiphile consists of a central hydrophilic component and two lipophilic components. The hydrophilic component is derived from, for example, polyglycols and the lipophilic components are derived from, for example fatty acids or aliphatic alcohols.

U.S. Pat. No. 5,262,233 discloses agricultural films which may have incorporated therein an anti-fogging agent which may be a poly(ethylene oxide) of a long chain alcohol.

U.S. Pat. No. 3,048,266 discloses polyolefin films with antifog properties which have incorporated therein esters or ethers of ethylene oxide adducts.

U.S. Pat. No. 5,001,015 discloses polyolefin films with antistatic properties which include as possible antistatic agents the reaction products of polyalkoxylates with fatty alcohols.

U.S. Pat. No. 4,304,234 discloses a method of increasing the wettability of polyolefin filaments by treatment with polar compounds such as adducts of propylene oxide and/or ethylene oxide.

U.S. Pat. No. 5,804,625 discloses the preparation of hydrophilic thermoplastic fibers that have incorporated therein one or more fluoroaliphatic group-containing nonionic surfactants and one or more nonionic, non-fluorinated, polyoxyethylene group-containing surfactants.

U.S. Pat. No. 6,239,047 discloses wettable polyolefin fibers which have incorporated therein a polyethylene glycol oleiyl ether additive.

U.S. Pat. No. 5,654,086 discloses hydrophilic thermoplastic fibers to which a surfactant mixture is adhered.

WO 00/28143 discloses a method for the hydrophilic finishing of polyolefin or polyester fibers in which a compound of the class of alkylethoxylates is employed.

EP 888786, EP 800833 and WO 0022061 each discusses adhesive compositions in nonwoven articles with improved wicking that contain surfactants such as ethoxylated monoalcohols.

WO 01/14621 discloses a biodisintegratable nonwoven material comprising an aliphatic polyester, polyolefin microfibers and a compatibilizer.

Atmer® 502, is described in a September, 1998 data sheet as having long-lasting antifog properties in LDPE agricultural film. Atmer® 502, an ethoxylated alcohol, is a trademark of Uniqema.

Unithox® 420 is described in a 1996 Technical Release of the Petrolite Corporation.

There remains a need for fabrics with improved wettability for use in sanitary articles, baby diapers, and the like. In particular, the need remains for improved wettability for hydrophobic polyolefin fabrics prepared from woven and nonwoven fibers and which have the required softness. The specific polyolefin compositions of the present invention have superior wettability properties.

DETAILED DISCLOSURE

The present invention pertains to a soft, wettable polyolefin fiber or filament, comprising a melt blend which comprises
(a) a polyolefin; and
(b) at least one compound of the formula (I)

wherein
$R_1$ is a straight or branched chain alkyl of 22 to 40 carbon atoms and the hydrophilic oligomer is a homo- or co-oligomer consisting of monomer units derived from monomers selected from the group consisting of ethylene oxide, propylene oxide, ethylene glycol, propylene glycol, epichlorhydrin, acrylic acid, methacrylic acid, ethylene imine, caprolactone, vinyl alcohol and vinyl acetate;

and wherein the hydrophilic oligomer consists of between 2 and 10 monomer units.

The hydrophilic oligomer consists of for example 2, 3, 4, 5, 6, 7, 8, 9 or 10 monomer units.

In compounds of formula (I) according to the present invention, $R_1$ is for example a straight or branched chain alkyl of 22, 23, 24, 25, 26, 27, 28, 29, 30, 31, 32, 33, 34, 35, 36, 37, 38, 39 or 40 carbon atoms.

The compound of formula (I) may be for example where the hydrophilic oligomer is derived from ethylene oxide, illustrated by a compound of formula (Ia):

where x is 2 to 10 and $R_1$ is a straight or branched chain alkyl of 22 to 40 carbon atoms. The term "x" is for example 2, 3, 4, 5, 6, 7, 8, 9 or 10.

The compound of formula (I) may be described as an AB diblock amphiphilic co-oligomer. The chain length of the alkyl of $R_1$ and the number of monomer units of the hydrophilic oligomer may be discrete values. Alternatively, for present compounds of formula (I), both the chain length of the alkyl of $R_1$ and the number of monomer units of the hydrophilic oligomer may be average values.

A specific example of a compound of formula (Ia) is where it is an ethoxylated aliphatic alcohol of formula (Ib) where $R_1$ is a straight chain alkyl with an average value of 30 carbon atoms and x has an average value of 2.5:

The compositions of the present invention may also comprise additive mixtures of two or more compounds of formula (I). The present compositions may also comprise other known amphiphilic additives. In particular the additional additives may be ethoxylated aliphatic alcohols such as Atmer® 502, a 2 mole ethoxylated stearyl alcohol, $C_{18}H_{37}(OCH_2CH_2)_2OH$, CAS #9005-00-9. Atmer® is a trademark of Uniqema. Atmer® 502 is an example of an ethoxylated aliphatic alcohol that is not of present formula (I).

The compound (Ib) is available from Baker Petrolite as Unithox® 420, CAS #97953-22-5.

The present compositions are prepared by melt extrusion processes to form fibers or filaments. In accordance with known technology such as continuous filament spinning for yarn or staple fiber, and nonwoven processes such as spunbond production and meltblown production, the fibers or filaments are formed by extrusion of the molten polymer through small orifices. In general, the fibers or filaments thus formed are then drawn or elongated to induce molecular orientation and affect crystallinity, resulting in a reduction in diameter and an improvement in physical properties. In nonwoven processes such as spunbonding and meltblowing, the fibers or filaments are directly deposited onto a foraminous surface, such as a moving flat conveyor and are at least partially consolidated by any of a variety of means including, but not limited to, thermal, mechanical or chemical methods of bonding. It is known to those skilled in the art to combine processes or the fabrics from different processes to produce composite fabrics which possess certain desirable characteristics. Examples of this are combining spunbond and meltblown to produce a laminate fabric that is best known as SMS, meant to represent two outer layers of spunbond fabric and an inner layer of meltblown fabric. Additionally either or both of these processes may be combined in any arrangement with a staple fiber carding process or bonded fabrics resulting from a nonwoven staple fiber carding process. In such described laminate fabrics, the layers are generally at least partially consolidated by one of the means listed above.

The invention is also applicable to melt extruded bi-component fibers, wherein one of the components is a polyolefin according to this invention.

Non-woven fabrics of polyolefin may have a carded fiber structure or comprise a mat in which the fibers or filaments are distributed in a random array. The fabric may be formed by any one of numerous known processes including hydroentanglement or spun-lace techniques, or by air laying or meltblowing filaments, batt drawing, stitchbonding, etc., depending upon the end use of the article to be made from the fabric.

Spunbond filament sizes most useful for wettable fabrics of the anticipated type are from about 1.0 to about 3.2 denier. Melblown fibers typically have a fiber diameter of less than 15 microns and most typically for the anticipated applications are fiber diameters less than 5 microns, ranging down to the submicron level. Webs in a composite construction may be processed in a wide variety of basis weights.

As described, thermoplastic polypropylene fibers, which are typically extruded at temperatures in the range of from about 210° to about 240° C., are inherently hydrophobic in that they are essentially non-porous and consist of continuous molecular chains incapable of attracting or binding to water molecules. As a result, untreated polypropylene fabrics, even while having an open pore structure, tend to resist the flow of liquids such as water or urine through the fabric, or from one surface to the other.

According to the present invention, a specific ethoxylated amphiphile of formula (I) is incorporated into a thermoplastic polyolefin, such as polypropylene, in the melt, and is extruded with the polyolefin into the form of fibers and filaments which are then quenched, attenuated and formed into fabrics, either in a subsequent or concomitant processing step.

The compound of formula (I) may be compounded with the polymer pellets which are to be melt extruded. To improve processing, the compound may be preformulated or compounded into a low MFR polypropylene which may also contain a small amount of inorganic powder, such as talc, and other traditional stabilizers.

The mixing of the compound of formula (I) into the polyolefin is done by mixing it into molten polymer by commonly used techniques such as roll-milling, mixing in a Banbury type mixer, or mixing in an extruder barrel and the like. The heat history (time at which held at elevated temperature) can be shortened by mixing the compound of formula (I) with unheated polymer particles so as to achieve substantially even distribution of the agent in the mass of polymer, thereby reducing the amount of time needed for intensive mixing at molten temperature.

Conveniently, the compound of formula (I) can also be added substantially simultaneously or sequentially with any other additives which may be desired in certain instances. The compound of formula (I) may also be preblended with other additives and the blend then added to the polymer. It is contemplated that in some instances a compound of formula (I) may have the additional benefit of aiding the other additives to become more easily or evenly dispersed or dissolved in the polyolefin. For easier batch-to-batch control of quality, it may be preferred to employ concentrated masterbatches of polymer/additive blends which are subsequently blended, as portions, to additional quantities of polymer to achieve the final desired formulation. The masterbatch, or the neat additives, may be injected into freshly prepared polymer while the polymer is still molten and after it leaves the polymerization vessel or train, and blended therewith before the molten polymer is chilled to a solid or taken to further processing.

The compounds of component (b), in total, are present in the compositions of this invention from about 0.1 % to about 15 % by weight, based on the weight of the polyolefin of component (a). For many applications, a typical amount of the compound of formula (I) is from about 1 % to about 7 % based on the weight of component (a).

The incorporation of a compound of formula (I) into a polyolefin fiber or filament according to the present invention results in observed improved wettability of these naturally hydrophobic materials. This modification is also durable, such that the fibers or filaments and fabrics made therefrom do not lose their wettability upon aging or handling. The improved wettability is stable to repeated insults, without a loss of performance, even over extended time periods.

The present invention is aimed at nonwoven fabrics, for example polypropylene fabrics. It is also aimed at threads or yarns for weaving or knitting in conventional textile processes.

The additives of the present invention are effective irrespective of other factors that influence the properties of nonwoven fabrics, for example, basis weight, fiber diameter, degree and type of bonding of the fibers, and the synergistic effects and influence of composite structures, such as the already describes SMS structures.

The present invention is not limited to single-component fibers. Polyolefin bi-component fibers, particularly side-by-side or sheath-core fibers of polypropylene and polyethylene would be expected to demonstrate the same practical benefits as single component fibers of either type. It would be particularly efficacious to include the melt additive only in the polyethylene component as that softer polymer could be expected to promote more efficient blooming of the present additives of formula (I) to the surface of that component fiber or filament.

The wettable fabrics produced from the fibers or filaments of this invention are particularly useful, for example, as the skin contacting inner lining fabric of sanitary articles, particularly single use diapers, training pants, feminine hygiene products or incontinence care products. The fabrics also have utility in wet and dry wipes, wound dressings, surgical capes, filter medial, battery separators, and the like.

The structure of diapers are described for example in U.S. Pat. Nos. 5,961,504, 6,031,147 and 6,110,849, all incorporated herein by reference.

In addition, it is often desirable to impart wettability to melt extruded polyolefin films. Such films, in perforated form, are widely used as cover sheets for sanitary articles.

For coverstock for sanitary articles, improvements in wetback properties can be improved by the use of two or more layers of fabric bonded together. Examples include two spunbond layers or an SMS fabric in which the meltblown layer is devoid of the additive of formula (I).

The fabrics of the present invention may be sterilized by exposure to about 0.5 to about 10 megarads of gamma irradiation. Sterilization with gamma irradiation is employed for hospital garments and the like.

Polyolefin woven and nonwoven fibers and fabrics prepared according to the present invention also exhibit exceptional printability. As a result of their inherent hydrophobic nature, polyolefin fibers and fabrics may exhibit problems towards printability, that is standard printing techniques. The compositions of the present invention overcome these problems as well.

Examples for polyolefins of component (a) are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, for example polyethylene and polypropylene, can be prepared by different, and especially by the following, methods:

i) radical polymerization (normally under high pressure and at elevated temperature).

ii) catalytic polymerization using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either p- or s-coordinated. These metal complexes may be in the free form or fixed on substrates, typically on activated magnesium chloride, titanium(III) chloride, alumina or silicon oxide. These catalysts may be soluble or insoluble in the polymerization medium. The catalysts can be used by themselves in the polymerization or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metallocene or single site catalysts (SSC).

2. Mixtures of the polymers mentioned under 1.), for example mixtures of polypropylene with polyisobutylene, polypropylene with polyethylene (for example PP/HDPE, PP/LDPE) and mixtures of different types of polyethylene (for example LDPE/HDPE).

3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylene/alkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.

Polyolefins of the present invention are for example polypropylene homo- and copolymers and polyethylene homo- and copolymers. For instance, polypropylene, high density polyethylene (HDPE), linear low density polyethylene (LLDPE) and polypropylene random and impact copolymers.

It is within the purview of the present invention to employ blends or alloys of olefin polymers.

The present polyolefin fibers, filaments and fabrics may also have incorporated or applied thereto appropriate additives such as ultraviolet light absorbers, hindered amine light stabilizers, antioxidants, processing aids and other additives.

For example, the compositions of the invention may optionally also contain from about 0.01 to about 10 %, preferably from about 0.025 to about 5 %, and especially from about 0.1 to about 3 % by weight of various conventional stabilizer coadditives, such as the materials listed below, or mixtures thereof.

1. Antioxidants 1.1. Alkylated monophenols, for example 2,6-di-tert-butyl-4-methylphenol, 2-tert-butyl-4,6-dimethylphenol, 2,6-di-tert-butyl4-ethylphenol, 2,6-di-tert-butyl-4-n-butylphenol, 2,6-di-tert-butyl-4-isobutylphenol, 2,6-dicyclopentyl4-methylphenol, 2-($\alpha$-methylcyclohexyl)4,6-dimethylphenol, 2,6-dioctadecyl-4-methylphenol, 2,4,6-tricyclohexylphenol, 2,6-di-tert-butyl-4-methoxymethylphenol, nonylphenols which are linear or branched in the side chains, for example, 2,6-di-nonyl-4-methylphenol, 2,4-dimethyl-6-(1-methylundec-1-yl)phenol, 2,4-dimethyl-6-(1-methylheptadec-1-yl)phenol, 2,4-dimethyl-6-(1-methyltridec-1-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Tocopherols, for example $\alpha$-tocopherol, $\beta$-tocopherol, $\gamma$-tocopherol, $\delta$-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl) disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-($\alpha$-methylcyclohexyl)phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-($\alpha$-methylbenzyl)-4-nonylphenol], 2,2'-methylenebis[6-($\alpha,\alpha$-dimethylbenzyl)4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)4-methylphenol, 1,1,3-tris(5-tert-butyl-4-hydroxy-2-methylphenyl)butane, 1,1-bis(5-tert-butyl4-hydroxy-2-methyl-phenyl)-3-n-dodecylmercaptobutane, ethylene glycol bis[3,3-bis(3-tert-butyl-4-hydroxyphenyl)butyrate], bis(3-tert-butyl-4-hydroxy-5-methyl-phenyl)dicyclopentadiene, bis[2-(3'tert-butyl-2-hydroxy-5-methylbenzyl)-6-tert-butyl4-methylphenyl]terephthalate, 1,1-bis-(3,5-dimethyl-2-hydroxyphenyl)butane, 2,2-bis-(3,5-di-tert-butyl4-hydroxyphenyl)propane, 2,2-bis-(5-tert-butyl 4-hydroxy2-methylphenyl)-4-n-dodecylmercaptobutane, 1,1,5,5-tetra-(5-tert-butyl-4-hydroxy-2-methylphenyl)pentane.

1.7. Benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, 1,3,5-tri-(3,5-di-tert-butyl-4-hydroxybenzyl)-2,4,6-trimethylbenzene, di-(3,5-di-tertbutyl4-hydroxybenzyl) sulfide, 3,5-di-tert-butyl-4-hydroxybenzyl-mercapto-acetic acid isooctyl ester, bis-(4-tert-butyl-3-hydroxy-2,6-dimethylbenzyl)dithiol terephthalate, 1,3,5-tris-(3,5-di-tert-butyl-4-hydroxybenzyl) isocyanurate, 1,3,5-tris-(4-tert-butyl-3-hydroxy-2,6-dimethylbenzyl) isocyanurate, 3,5-di-tert-butyl-4-hydroxybenzyl-phosphoric acid dioctadecyl ester and 3,5-di-tert-butyl-4-hydroxybenzyl-phosphoric acid monoethyl ester, calcium-salt.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl4-hydroxybenzyl)malonate, bis[4-(1,1,3,3-tetramethylbutyl)phenyl]-2,2-bis(3,5-di-tert-butyl4-hydroxybenzyl) malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3, 5-di-tert-butyl4-hydroxybenzyl)phenol.

1.10. Triazine compounds, for example 2,4-bis(octylmercapto)-6-(3,5-di-tert-butyl-4-hydroxyanilino)-1,3,5-triazine, 2-octylmercapto4,6-bis(3,5-di-tert-butyl-4-hydroxyanilino)-1,3,5-triazine, 2-octylmercapto-4,6-bis(3,5-di-tert-butyl4-hydroxyphenoxy)-1,3,5-triazine, 2,4,6-tris-(3,5-di-tert-butyl-4-hydroxyphenoxy)-1,2,3-triazine, 1,3,5-tris-(3,5-di-tert-butyl4-hydroxy-benzyl)isocyanurate, 1,3,5-tris(4-tert-butyl-3-hydroxy-2,6-dimethylbenzyl)isocyanurate, 2,4,6-tris(3, 5-di-tert-butyl-4-hydroxyphenylethyl)-1,3,5-triazine, 1,3,5-tris(3,5-di-tert-butyl4-hydroxy-phenylpropionyl)-hexahydro-1,3,5-triazine, 1,3,5-tris(3,5-dicyclohexyl4-hydroxybenzyl)isocyanurate.

1.11. Benzvlphosphonates, for example dimethyl-2,5-di-tert-butyl-4-hydroxybenzylphosphonate, diethyl-3,5-di-tert-butyl4-hydroxybenzylphosphonate, dioctadecyl3,5-di-tert-butyl-4-hydroxybenzylphosphonate, dioctadecyl-5-tert-butyl4-hydroxy-3-methylbenzylphosphonate, the calcium salt of the monoethyl ester of 3,5-di-tert-butyl4-hydroxybenzylphosphonic acid.

1.12. Acylaminophenols, for example 4-hydroxy-lauric acid anilide, 4-hydroxy-stearic acid anilide, 2,4-bis-octylmercapto-6-(3,5-di-tert-butyl-4-hydroxyanilino)-s-triazine and octyl-N-(3,5-di-tert-butyl4-hydroxyphenyl)-carbamate.

1.13. Esters of β-(3,5-di-tert-butyl-4-hydroxyphenyl)propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane.

1.14. Esters of β-(5-tert-butyl-4-hydroxy-3-methylphenyl) propionic acid with mono- or polyhydric alcohols, e.g. with methanol, ethanol, n-octanol, i-octanol, octadecanol, 1,6-hexane-diol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis-(hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane.

1.15. Esters of β-(3.5-dicyclohexyl-4-hydroxyphenyl)propionic acid with mono- or polyhydric alcohols, e.g. with methanol, ethanol, octanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis (hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis (hydroxyethyl)oxamide, 3-thiaundecanol, 3-thiapentadecanol, trimethylhexanediol, trimethylolpropane, 4-hydroxymethyl-1-phospha-2,6,7-trioxabicyclo [2.2.2]octane.

1.17. Amides of β-(3,5-di-tert-butyl-4-hydroxphenyl)propionic acid e.g. N,N'-bis(3,5-di-tert-butyl-4-hydroxyphenylpropionyl)hexamethylenediamide, N,N'-bis(3,5-di-tert-butyl-4-hydroxyphenylpropionyl)trimethylenediamide, N N'-bis(3, 5-di-tert-butyl-4-hydroxyphenylpropionyl)hydrazide, N,N'-bis[2-(3-[3,5-di-tert-butyl4-hydroxyphenyl] propionyloxy)ethyl]oxamide (Naugard® XL-1 supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N, N'-bis(1,4-dimethylpentyl)-p-phenylenediamine, N, N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenlenediamine, 4-(p-toluenesulfamoyl)diphenylamine, N, N'-dimethyl-N, N'-di-sec-butyl-p-phenylenediamine, diphenylamine, N-allyidiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyidiphenylamine, 4-n-butylaminophenol, 4-butyrylaminophenol, 4-nonanoylaminophenol, 4-dodecanoylaminophenol, 4-octadecanoylaminophenol, bis (4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino] ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyl-diphenylamines, a mixture of mono- and dialkylated nonyidiphenylamines, a mixture of mono- and dialkylated dodecyidiphenylamines, a mixture of mono- and dialkylated isopropyl/isohexyldiphenylamines, a mixture of mono- and dialkylated tert-butyldiphenylamines, 2,3-dihydro-3,3-dimethyl4H-1,4-benzothiazine, phenothiazine, a mixture of mono- and dialkylated tert-butyl/tert-octylphenothiazines, a mixture of mono- and dialkylated tert-octyl-phenothiazines, N-allylphenothiazin, N,N,N', N'-tetraphenyl-1,4-diaminobut-2-ene, N, N-bis-(2,2,6,6-tetramethyl-piperid-4-yl-hexamethylenediamine, bis(2,2,6,6-tetramethylpiperid-4-yl)-sebacate, 2,2,6,6-tetramethylpiperidin4-one, 2,2,6,6-tetramethylpiperidin-4-ol.

2. UV Absorbers and Light Stabilizers 2.1. 2-(2-Hydroxyphenyl)-2H-benzotriazoles, for example known commercial hydroxyphenyl-2H-benzotriazoles and benzotriazoles as disclosed in, U.S. Pat. Nos. 3,004,896; 3,055,896; 3,072,585; 3,074,910; 3,189,615; 3,218,332; 3,230,194; 4,127,586; 4,226,763; 4,275,004; 4,278,589; 4,315,848; 4,347,180; 4,383,863; 4,675,352; 4,681,905; 4,853,471; 5,268,450; 5,278,314; 5,280,124; 5,319,091; 5,410,071; 5,436,349; 5,516,914; 5,554,760; 5,563,242; 5,574,166; 5,607,987 and 5,977,219, such as 2-(2-hydroxy-5-methylphenyl)-2H-benzotriazole, 2-(3,5-di-t-butyl-2-hydroxyphenyl)-2H-benzotriazole, 2-(2-hydroxy-5-t-butylphenyl)-2H-benzotriazole, 2-(2-hydroxy-5-t-octylphenyl)-2H-benzotriazole, 5-chloro-2-(3,5-di-t-butyl-2-hydroxyphenyl)-2H-benzotriazole, 5-chloro-2-(3-t-butyl-2-hydroxy-5-methylphenyl)-2H-benzotriazole, 2-(3-sec-butyl-5-t-butyl-2-hydroxyphenyl)-2H-benzotriazole, 2-(2-hydroxy-4-octyloxyphenyl)-2H-benzotriazole, 2-(3,5-di-t-amyl-2-hydroxyphenyl)-2H-benzotriazole, 2-(3,5-bis-α-cumyl-2-hydroxyphenyl)-2H-benzotriazole, 2-(3-t-butyl-2-hydroxy-5-(2-(ω-hydroxy-octa-(ethyleneoxy)carbonyl-ethyl)-, phenyl)-2H-benzotriazole, 2-(3-dodecyl-2-hydroxy-5-methylphenyl)-2H-benzotriazole, 2-(3-t-butyl-2-hydroxy-5-(2-octyloxycarbonyl)ethylphenyl)-2H-benzotriazole, dodecylated 2-(2-hydroxy-5-methylphenyl)-2H-benzotriazole, 2-(3-t-butyl-2-hydroxy-5-(2-octyloxycarbonylethyl)phenyl)-5-chloro-2H-benzotriazole, 2-(3-tert-butyl-5-(2-(2-ethylhexyloxy)-carbonylethyl)-2-hydroxyphenyl)-5-chloro-2H-benzotriazole, 2-(3-t-butyl-2-hydroxy-5-(2-methoxycarbonylethyl)phenyl)-5-chloro-2H-benzotriazole, 2-(3-t-butyl-2-hydroxy-5-(2-methoxycarbonylethyl)phenyl)-2H-benzotriazole, 2-(3-t-butyl-5-(2-(2-ethylhexyloxy)carbonylethyl)-2-hydroxyphenyl)-2H-benzotriazole, 2-(3-t-butyl-2-hydroxy-5-(2-isooctyloxycarbonylethyl)phenyl-2H-benzotriazole, 2,2'-methylene-bis(4-t-octyl-(6-2H-benzotriazol-2-yl)phenol), 2-(2-hydroxy-3-α-cumyl-5-t-octylphenyl)-2H-benzotriazole, 2-(2-hydroxy-3-t-octyl-5-α-cumylphenyl)-2H-benzotriazole, 5-fluoro-2-(2-hydroxy-3, 5-di-α-cumyl-phenyl)-2H-benzotriazole, 5-chloro-2-(2-hydroxy-3,5-di-α-cumylphenyl)-2H-benzotriazole, 5-chloro-2-(2-hydroxy-3-α-cumyl-5-t-octylphenyl)-2H-benzotriazole, 2-(3-t-butyl-2-hydroxy-5-(2-isooctyloxycarbonylethyl)phenyl)-5-chloro-2H-benzotriazole, 5-trifluoromethyl-2-(2-hydroxy-3-α-cumyl-5-t-octylphenyl)-2H-benzotriazole, 5-trifluoromethyl-2-(2-hydroxy-5-t-octylphenyl)-2H-benzotriazole, 5-trifluoromethyl-2-(2-hydroxy-3,5-di-t-octylphenyl)-2H-benzotriazole, methyl 3-(5-trifluoromethyl-2H-benzotriazol-2-yl)-5-t-butyl-4-hydroxyhydrocinnamate, 5-butylsulfonyl-2-(2-hydroxy-3-α-cumyl-5-t-octylphenyl)-2H-benzotriazole, 5-trifluoromethyl-2-(2-hydroxy-3-α-cumyl-5-t-butylphenyl)-2H-benzotriazole, 5-trifluoromethyl-2-(2-hydroxy-3,5-di-t-butylphenyl)-2H-benzotriazole, 5-trifluoromethyl-2-(2-hydroxy-3,5-di-α-cumylphenyl)-2H-benzotriazole, 5-butylsulfonyl-2-(2-hydroxy-3,5-di-t-butylphenyl)-2H-benzotriazole and 5-phenylsulfonyl-2-(2-hydroxy-3, 5-di-t-butylphenyl)-2H-benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutyl-phenyl salicylate, phenyl salicylate, octylphenyl salicylate, dibenzoyl resorcinol, bis(4-tertbutylbenzoyl) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzoate, 2-methyl4,6-di-tert-butylphenyl 3,5-di-tert-butyl4-hydroxybenzoate.

2.4. Acrylates and malonates, for example, α-cyano-β,β-diphenylacrylic acid ethyl ester or isooctyl ester, α-carbomethoxy-cinnamic acid methyl ester, α-cyano-β-methyl-p-methoxy-cinnamic acid methyl ester or butyl ester, α-carbomethoxy-p-methoxy-cinnamic acid methyl ester, N-(β-carbomethoxy-β-cyanovinyl)-2-methyl-indoline, Sanduvor® PR25, dimethyl p-methoxybenzylidenemalonate (CAS#7443-25-6), and Sanduvor® PR31, di-(1,2,2,6,6-pentamethylpiperidin-4-yl) p-methoxybenzylidenemalonate (CAS #147783-69-5).

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyldithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy4-methylphenyl undecylketoxime, nickel complexes of 1-phenyl-4-lauroyl-5-hydroxypyrazole, with or without additional ligands.

2.6. Sterically hindered amine stabilizers, for example 4-hydroxy-2,2,6,6-tetramethylpiperidine, 1-allyl4-hydroxy-2,2,6,6-tetramethylpiperidine, 1-benzyl4-hydroxy-2,2,6,6-tetramethylpiperidine, bis(2,2,6,6-tetramethyl4-piperidyl) sebacate, bis(2,2,6,6-tetramethyl-4-piperidyl) succinate, bis (1,2,2,6,6-pentamethyl-4-piperidyl) sebacate, bis(1-octyloxy-2,2,6,6-tetramethyl-4-piperidyl) sebacate, bis(1,2,2,6, 6-pentamethyl4-piperidyl) n-butyl-3,5-di-tert-butyl4-hydroxybenzylmalonate, the condensate of 1-(2-hydroxyethyl)-2,2,6,6-tetramethyl4-hydroxypiperidine and succinic acid, linear or cyclic condensates of N,N'-bis(2,2,6, 6-tetramethyl-4-piperidyl)hexamethylenediamine and 4-tert-octylamino-2,6-dichloro-1,3,5-triazine, tris(2,2,6,6-tetramethyl-4-piperidyl) nitrilotriacetate, tetrakis(2,2,6,6-tetramethyl-4-piperidyl)-1 ,2,3,4-butane-tetracarboxylate, 1,1'-(1 ,2-ethanediyl)-bis(3,3,5,5-tetramethylpiperazinone), 4-benzoyl-2,2,6,6-tetramethylpiperidine, 4-stearyloxy-2,2,6, 6-tetramethylpiperidine, bis(1,2,2,6,6-pentamethylpiperidyl)-2-n-butyl-2-(2-hydroxy-3,5-di-tert-butylbenzyl) malonate, 3-n-octyl-7,7,9,9-tetramethyl-1,3,8-triazaspiro [4.5]decan-2,4-dione, bis(1-octyloxy-2,2,6,6-tetramethylpiperidyl) sebacate, bis(1-octyloxy-2,2,6,6-tetramethyl-piperidyl) succinate, linear or cyclic condensates of N,N'-bis-(2, 2,6,6-tetramethyl-4-piperidyl)-hexamethylenediamine and 4-morpholino-2,6-dichloro-1,3,5-triazine, the condensate of 2-chloro4,6-bis(4-n-butylamino-2,2,6,6-tetramethylpiperidyl )-1,3,5-triazine and 1,2-bis(3-amino-propylamino) ethane, the condensate of 2-chloro4,6-di-(4-n-butylamino-1, 2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl4-piperidyl)pyrrolidin-2,5-dione, 3-dodecyl-1-(1,2,2,6,6-pentamethyl4-piperidyl)pyrrolidine-2,5-dione, a mixture of 4-hexadecyloxy- and 4-stearyloxy-2,2,6,6-tetramethylpiperidine, a condensation product of N,N'-bis(2,2,6,6-tetramethyl-4-piperidyl)hexamethylenediamine and 4-cyclohexylamino-2,6-dichloro-1,3,5-triazine, a condensation product of 1,2-bis(3-aminopropylamino)ethane and 2,4,6-trichloro-1,3,5-triazine as well as 4-butylamino-2,2,6,6-tetramethylpiperidine (CAS Reg. No. [136504-96-6]); N-(2,2,6,6-tetramethyl4-piperidyl)-n-dodecylsuccinimid, N-(1,2,2,6,6-pentamethyl-4-piperidyl)-n-dodecylsuccinimid, 2-undecyl-7,7,9,9-tetramethyl-1-oxa-3, 8-diaza-4-oxo-spiro[4,5]decane, a reaction product of 7,7,9, 9-tetramethyl-2-cycloundecyl-1-oxa-3,8-diaza-4-oxospiro [4,5]decane and epichlorohydrin, 1,1-bis(1,2,2,6,6-pentamethyl4-piperidyloxycarbonyl)-2-(4-methoxyphenyl)ethene, N, N'-bis-formyl-N,N'-bis(2,2,6,6-tetramethyl-4-piperidyl) hexamethylenediamine, diester of 4-methoxy-methylene-malonic acid with 1,2,2,6,6-pentamethyl4-hydroxypiperidine, poly[methylpropyl-3-oxy4-(2,2,6,6-tetramethyl4-piperidyl)]siloxane, reaction product of maleic acid anhydride-α-olefin-copolymer with 2,2,6,6-tetramethyl4-aminopiperidine or 1,2,2,6,6-pentamethyl4-aminopiperidine.

The sterically hindered amine may also be one of the compounds described in GB-A-2301106 as component I-a), I-b), I-c), I-d), I-e), I-f), I-g), I-h), I-i), I-j), I-k) or I-l), in particular the light stabilizer 1-a-1, 1-a-2, 1-b-1, 1-c-1, 1-c-2, 1-d-1, 1-d-2, 1-d-3, 1-e-1, 1-f-1, 1-g-1, 1-g-2 or 1-k-1 listed on pages 68 to 73 of said GB-A-2301106.

The sterically hindered amine may also be one of the compounds described in EP 782994, for example compounds as described in claims 10 or 38 or in Examples 1-12 or D-1 to D-5 therein.

2.7. Sterically hindered amines substituted on the N-atom by a hydroxy-substituted alkoxy group, for example compounds such as 1-(2-hydroxy-2-methylpropoxy)-4-octadecanoyloxy-2,2,6,6-tetramethylpiperidine, 1-(2-hydroxy-2-methylpropoxy)-4-hexadecanoyloxy-2,2,6,6-tetramethylpiperidine, the reaction product of 1-oxyl-4-hydroxy-2,2,6,6-tetramethylpiperidine with a carbon radical from t-amylalcohol, i-(2-hydroxy-2-methylpropoxy)-4-hydroxy-2,2,6,6-tetramethylpiperidine, 1-(2-hydroxy-2-methylpropoxy)4-oxo-2,2,6,6-tetramethylpiperidine, bis(1-(2-hydroxy-2-methylpropoxy)-2,2,6,6-tetramethylpiperidin-4-yl) sebacate, bis(1-(2-hydroxy-2-methylpropoxy)-2,2,6,6-tetramethylpiperidin4-yl) adipate, bis(1-(2-hydroxy-2-methylpropoxy)-2,2,6,6-tetramethylpiperidin-4-yl) succinate, bis(1-(2-hydroxy-2-methylpropoxy)-2,2,6,6-tetramethylpiperidin4-yl) glutarate and 2,4-bis{N-[1-(2-hydroxy-2-methylpropoxy)-2,2,6,6-tetramethylpiperidin-4-yl]-N-butylamino}-6-(2-hydroxyethyl-amino)-s-triazine.

2.8. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'-ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.9. Tris-aryl-o-hydroxyphenyl-s-triazines, for example known commercial tris-aryl-o-hydroxyphenyl-s-triazines and triazines as disclosed in, WO 96/28431, EP 434608, EP 941989, GB 2,317,893, U.S. Pat. Nos. 3,843,371; 4,619,956; 4,740,542; 5,096,489; 5,106,891; 5,298,067; 5,300,414; 5,354,794; 5,461,151; 5,476,937; 5,489,503; 5,543,518; 5,556,973; 5,597,854; 5,681,955; 5,726,309; 5,942,626; 5,959,008; 5,998,116 and 6,013,704, for example 4,6-bis-(2,4-dimethylphenyl)-2-(2-hydroxy-4-octyloxyphenyl)-s-triazine, Cyasorb® 1164, Cytec Corp, 4,6-bis-(2,4-dimethylphenyl)-2-(2,4-dihydroxyphenyl)-s-triazine, 2,4-bis(2,4-dihydroxyphenyl)-6-(4-chlorophenyl)-s-triazine, 2,4-bis[2-hydroxy-4-(2-hydroxy-ethoxy)phenyl]-6-(4-chlorophenyl)-s-triazine, 2,4-bis[2-hydroxy4-(2-hydroxy-4-(2-hydroxy-ethoxy)phenyl]-6-(2,4-dimethylphenyl)-s-triazine, 2,4-bis [2-hydroxy4-(2-hydroxyethoxy)phenyl]-6-(4-bromophenyl)-s-triazine, 2,4-bis[2-hydroxy-4-(2-acetoxyethoxy)phenyl]-6-(4-chlorophenyl)-s-triazine, 2,4-bis(2,4-dihydroxyphenyl)-6-(2,4-dimethylphenyl)-s-triazine, 2,4-bis(4-biphenylyl)-6-(2-hydroxy-4-octyloxycarbonylethylideneoxyphenyl)-s-triazine, 2-phenyl-4-[2-hydroxy-4-(3-sec-butyloxy-2-hydroxypropyloxy)phenyl]-6-[2-hydroxy4-(3-sec-amyloxy-2-hydroxypropyloxy)-phenyl]-s-triazine, 2,4-bis(2,4-dimethylphenyl)-6-[2-hydroxy4-(3-benzyloxy-2-hydroxy-propyloxy) phenyl]-s-triazine, 2,4-bis(2-hydroxy4-n-butyloxyphenyl)-6-(2,4-di-n-butyloxyphenyl)-s-triazine, 2,4-bis(2,4-dimethylphenyl)-6-[2-hydroxy-4-(3-nonyloxy*-2-hydroxypropyloxy)-5-α-cumylphenyl]-s-triazine (* denotes a mixture of octyloxy, nonyloxy and decyloxy groups), methylenebis-{2,4-bis(2,4-dimethylphenyl)-6-[2-hydroxy-4-(3-butyloxy-2-hydroxypropoxy)-phenyl]-s-triazine}, methylene bridged dimer mixture bridged in the 3:5', 5:5' and 3:3' positions in a 5:4:1 ratio, 2,4,6-tris(2-hydroxy-4-isooctyloxycarbonylisopropylideneoxyphenyl)-s-triazine, 2,4-bis(2,4-dimethylphenyl)-6-(2-hydroxy-4-hexyloxy-5-α-cumylphenyl)-s-triazine, 2-(2,4,6-trimethylphenyl)-4,6-bis[2-hydroxy-4-(3-butyloxy-2-hydroxypropyloxy)phenyl]-s-triazine, 2,4,6-tris[2-hydroxy-4-(3-sec-butyloxy-2-hydroxypropyloxy)phenyl]-s-triazine, mixture of 4,6-bis-(2,4-dimethylphenyl)-2-(2-hydroxy-4-(3-dodecyloxy-2-hydroxypropoxy)-phenyl)-s-triazine and 4,6-bis-(2,4-dimethylphenyl)-2-(2-hydroxy-4-(3-tridecyloxy-2-hydroxypropoxy)-phenyl)-s-triazine, Tinuvin® 400, Ciba Specialty Chemicals Corp., 4,6-bis-(2,4-dimethylphenyl)-2-(2-hydroxy-4-(3-(2-ethylhexyloxy)-2-hydroxypropoxy)-phenyl)-s-triazine and 4,6-diphenyl-2-(4-hexyloxy-2-hydroxyphenyl)-s-triazine.

3. Metal deactivators, for example N,N'-diphenyloxamide, N-salicylal-N'-salicyloyl hydrazine, N,N'-bis(salicyloyl) hydrazine, N, N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl)oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris (2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl) pentaerythritol diphosphite, bis(2,4,6-tris(tert-butylphenyl) pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-dibenzo[d,f][1,3,2]dioxaphosphepin, 6-fluoro-2,4,8,10-tetra-tert-butyl-12-methyl-dibenzo[d,g][1,3,2]dioxaphosphocin, bis(2,4-di-tert-butyl-6-methylphenyl) methyl phosphite, bis(2,4-di-tert-butyl-6-methylphenyl) ethyl phosphite, 2,2',2"-nitrilo [triethyltris(3,3',5,5'-tetra-tert-butyl-1,1'-biphenyl-2,2'-diyl) phosphite], 2-ethylhexyl(3,3',5,5'-tetra-tert-butyl-1,1'-biphenyl-2,2'-diyl)phosphite.

Especially preferred are the following phosphites:
Tris(2,4-di-tert-butylphenyl) phosphite (Irgafos® 168, Ciba Specialty Chemicals Corp.), tris(nonylphenyl) phosphite,

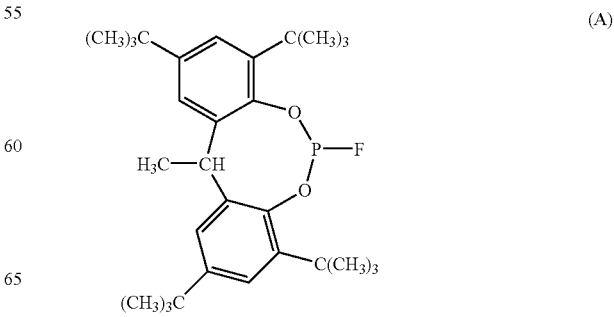

(A)

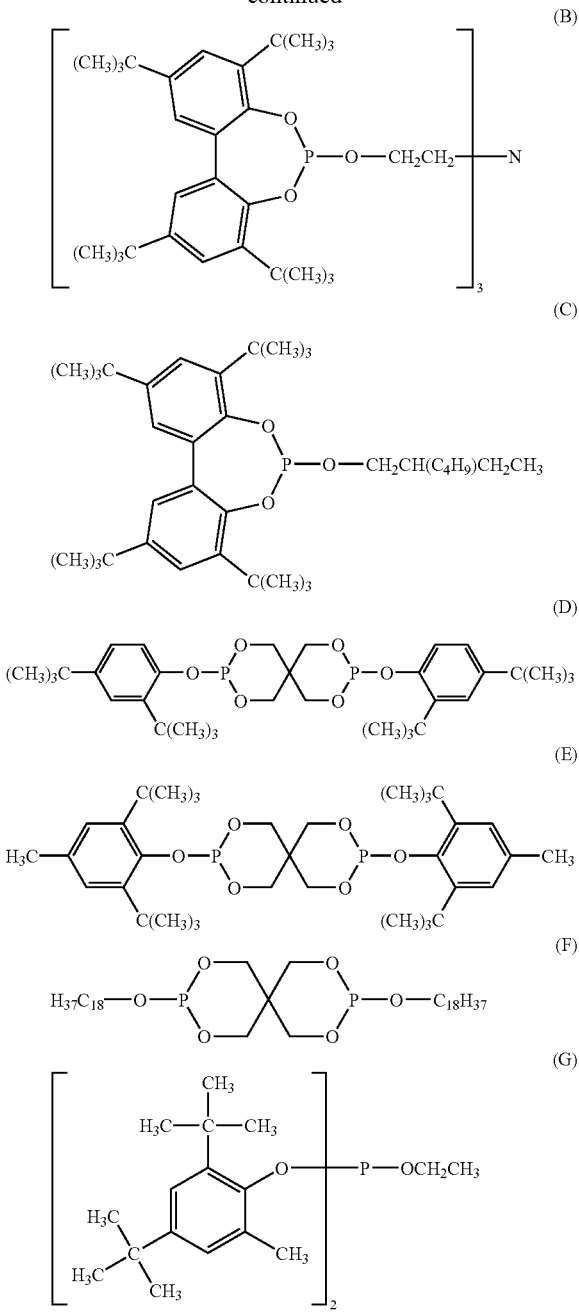

5. Hydroxylamines, for example N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N-methyl-N-octadecylhydroxylamine and the N,N-dialkylhydroxylamine derived from hydrogenated tallow amine.

6. Nitrones, for example N-benzyl-α-phenylnitrone, N-ethyl-α-methylnitrone, N-octyl-α-heptylnitrone, N-lauryl-α-undecylnitrone, N-tetradecyl-α-tridcylnitrone, N-hexadecyl-α-pentadecyinitrone, N-octadecyl-α-heptadecylnitrone, N-hexadecyl-α-heptadecylnitrone, N-ocatadecyl-α-pentadecylnitrone, N-heptadecyl-α-heptadecylnitrone, N-octadecyl-α-hexadecylnitrone, N-methyl-α-heptadecylnitrone and the nitrone derived from N,N-dialkylhydro-xylamine derived from hydrogenated tallow amine.

7. Amine oxides, for example amine oxide derivatives as disclosed in U.S. Pat. Nos. 5,844,029 and 5,880,191, didecyl methyl amine oxide, tridecyl amine oxide, tridodecyl amine oxide and trihexadecyl amine oxide.

8. Benzofuranones and indolinones, for example those disclosed in U.S. Pat. Nos. 4,325,863, 4,338,244, 5,175,312, 5,216,052, 5,252,643; DE-A4316611; DE-A-4316622; DE-A-4316876; EP-A-0589839 or EP-A-0591 102 or 3-[4-(2-acetoxyethoxy)-phenyl]-5,7-di-tert-butyl-benzofuran-2-one, 5,7-di-tert-butyl-3-[4-(2-stearoyloxyethoxy)phenyl]-benzofuran-2-one, 3,3'-bis[5,7-di-tert-butyl-3-(4-[2-hydroxyethoxy]phenyl)benzofuran-2-one], 5,7-di-tert-butyl-3-(4-ethoxyphenyl)benzofuran-2-one, 3-(4-acetoxy-3,5-dimethylphenyl)-5,7-di-tert-butyl-benzofuran-2-one, 3-(3,5-dimethyl-4-pivaloyloxyphenyl)-5,7-di-tert-butyl-benzofuran-2-one, 3-(3,4-dimethylphenyl)-5,7-di-tert-butyl-benzofuran-2-one, Irganox® HP-136, Ciba Specialty Chemicals Corp., and 3-(2,3-dimethylphenyl)-5,7-di-tert-butyl-benzofuran-2-one.

9. Thiosynergists, for example dilauryl thiodipropionate or distearyl thiodipropionate.

10. Peroxide scavengers, for example esters of β-thiodipropionic acid, for example the lauryl, stearyl, myristyl or tridecyl esters, mercaptobenzimidazole or the zinc salt of 2-mercapto-benzimidazole, zinc dibutyldithiocarbamate, dioctadecyl disulfide, pentaerythritol tetrakis(β-dodecylmercapto)propionate.

11. Polyamide stabilizers, for example copper salts in combination with iodides and/or phosphorus compounds and salts of divalent manganese.

12. Basic co-stabilizers, for example melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids, for example, calcium stearate, zinc stearate, magnesium behenate, magnesium stearate, sodium ricinoleate and potassium palmitate, antimony pyrocatecholate or zinc pyrocatecholate.

13. Nucleating agents, for example inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers).

14. Fillers and reinforcing agents, for example calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

15. Dispersing Agents, such as polyethylene oxide waxes or mineral oil.

16. Other additives, for example plasticizers, lubricants, emulsifiers, pigments, dyes, optical brighteners, rheology additives, catalysts, flow-control agents, slip agents, crosslinking agents, crosslinking boosters, halogen scavengers, smoke inhibitors, flameproofing agents, antistatic agents, clarifiers such as substituted and unsubstituted bis-benzylidene sorbitols, benzoxazinone UV absorbers such as 2,2'-p-phenylene-bis(3,1-benzoxazin-4-one), Cyasorb® 3638 (CAS#18600-59-4), and blowing agents.

It is also contemplated that the melt blends of the present invention may be formed into efficient microporous membranes, perforated films, or nets. That is, other wettable polyolefin articles that are not fibers, filaments or fabrics.

The following examples are for illustrative purposes only and are not to be construed as limiting the instant invention in any manner whatsoever. Additive levels are reported in weight percent.

EXAMPLE 1

Polypropylene Nonwoven Fiber

A dry mixture of 8.5 kg of polypropylene pellets, Exxon Polybond 3155 PP, and 1.5 kg of the compound of formula (Ib)

$$CH_3CH_2(CH_2CH_2)_{13}CH_2CH_2(OCH_2CH_2)_{2.5}OH \quad (Ib)$$

is prepared using a TURBULA Mixer Type TIOB. The 15 % concentrate mix is melt compounded using a Leistritz MIC 27/GL-32D twin screw extruder. The extruder heat zones are 190-220° C., screw speed 400 RPM and feeder speed 25 RPM. The molten polymer and additive exit via a two orifice round dye. The molten material is immediately cooled and solidified in a cold water trough. The solidified strand is fed into a CONAIR/JETRO 304 Pelletizer.

The compound of formula (Ib) is UNITHOX 420, available from Baker Petrolite.

The concentrate pellets are let down with 40 kg of additional Exxon Polybond 3155 PP pellets and are mixed with a Marion SPS 1224 mixer, resulting in an additive concentration of 3% by weight.

Nonwoven polypropylene fibers are prepared from the 3% additive pellets prepared as above using a REICOFIL II Spunbonder, under the following conditions:
Extruder temperature of 200-215° C.,
screen changer temperature of 205° C.,
spin pump temperature of 215° C. and speed of 18.6 rpm,
4,000 hole spinneret with a temperature gradient of 223-240° C.,
bonder pressure of 291 PSI with the lower roll at 138° C. and the upper roll at 140° C.,
cooling air speed of 3020 rpm and suction air speed of 2510 rpm, and
collection take up speed is adjusted to produce a nonwoven with a weight of 20 g/m².

The resultant nonwovens are evaluated for permeability and durability by measuring the liquid strike through time, the time for a known volume of simulated urine (9.0 g NaCl/L) to pass through the nonwoven. The INDA (International Nonwovens & Disposables Association) standard test method is #IST 70.3 (98) using a Lenzing Lister model 1997. Results are below.

The samples are also evaluated for continuous strike through and time delay multi strike through, again using the Lenzing Lister apparatus. Shorter time periods represent a desired faster liquid pass through. Results are below.

Finally, the samples are evaluated for their capacity to absorb simulated urine using INDA standard test method #IST 10.1 (95) part 8. This method is also used to measure the time delay absorbance capacity. The absorptive capacity is the ratio of the liquid weight held by the sample to the weight of the dry sample. Results are found below.

INDA Liquid Strike Through Time
Test Method #IST 70.3(98), results in seconds

| Blank (no additive) | 3% additive of formula (Ib) |
|---|---|
| >1,000 sec | 3.63 sec |
| >1,000 | 3.64 |
| | 4.21 |

Results of this test demonstrate that the present compositions provide a nonwoven polypropylene with excellent wettability.

Continuous Strike Through
Maximum 30 seconds between passes, results in seconds, tests on three identical nonwoven samples with 3% additive of formula (Ib).

| Pass 1 | Pass 2 | Pass 3 | Pass 4 | Pass 5 | Pass 6 | Pass 7 | Pass 8 | Pass 9 |
|---|---|---|---|---|---|---|---|---|
| 4.40 | 4.53 | 4.26 | 4.63 | 4.25 | 4.72 | 4.99 | 5.00 | 5.50 |
| 2.55 | 3.42 | 3.98 | 4.14 | 4.43 | 4.46 | 4.53 | 4.82 | 5.08 |
| 3.41 | 3.71 | 3.79 | 3.99 | 3.98 | 4.72 | 4.63 | 4.35 | 4.97 |

Results of the continuous strike through test demonstrate that the compositions of the present invention are effective towards passing through repeated liquid insults with short time periods in between. It is a demonstration of the durability or permanence of the additive of formula (Ib).

Time Delay Multi Strike Through
Dry one hour between passes, results in seconds, tests on five identical nonwoven samples each with 3% additive of formula (Ib).

| 0 hours | 1 hours | 2 hours | 3 hours | 4 hours | 5 hours | 6 hours | 7 hours |
|---|---|---|---|---|---|---|---|
| 6.99 | 5.00 | 3.95 | 5.28 | 0.56 | 3.40 | 2.59 | 2.99 |
| 7.24 | 5.67 | 5.81 | 4.54 | 4.82 | 3.68 | 3.96 | 3.13 |
| 6.00 | 4.73 | 4.53 | 2.53 | 3.81 | 3.42 | 3.98 | 3.04 |
| 9.93 | 6.50 | 4.81 | 4.92 | 3.96 | 3.99 | 4.24 | 4.71 |
| 4.68 | 4.17 | 5.02 | 3.20 | 3.17 | 3.57 | 2.98 | 2.54 |

Results of the time delay multi strike through test demonstrate that the compositions of the present invention are effective towards passing through repeated liquid insults with long time periods in between. It is a demonstration of the durability or permanence of the additive of formula (Ib).

Absorbance Capacity
INDA standard test #10.1(95) part 8, result is the ratio of weight of the simulated urine held by the sample to the weight of the dry sample.

| Blank - no additive: 0.4 | 3% additive of formula (Ib): 8.8 |
|---|---|

These results demonstrate the surprising hydrophilicity of compositions of the present invention.

Time Delay Absorbance Capacity

INDA standard test #10.1 (95) part 8, samples are saturated with simulated urine, air-dried for 24 hours, and saturated again. Result is the percent retained of the original ratio of the weight of the simulated urine held by the sample to the weight of the dry sample. Tests performed on nonwoven sample with 3% additive of formula (Ib).

| 24 hours | 48 hours | 72 hours | 96 hours |
|---|---|---|---|
| 75% | 61% | 61% | 58% |

These results demonstrate that the compositions of the present invention effectively maintain their hydrophilicity after multiple exposures to simulated urine.

EXAMPLE 2

Polypropylene Printability

Polypropylene, and 5% by weight of the additive of formula (Ib) are melt blended and spun into filaments and tufted into a carpet. The carpets are printed with a mixture of color index (C.I.) Acid Yellow 216:1, C.I. Acid Red 266 and C.I. Acid Blue 40 to have a dark brown trichromatic color. The printing paste also contains a thickener such as gaur gum. After printing, the applied amount of dyestuff is fixed in a steamer. After fixation, the carpet is rinsed with cold water. Carpets prepared with fibers of the present invention exhibit excellent printability.

EXAMPLE 3

Polypropylene Nonwoven Fiber

Example 1 is repeated replacing the compound of formula (Ib) with a 1:1 mixture of the compound of formula (Ib) and Atmer® 502, 2 mole ethoxylated stearyl alcohol. Excellent results are found for liquid strike through time, continuous strike through, time delay multi strike through and time delay absorbance capacity tests.

EXAMPLE 4

Alkaline Battery Separator—Percent KOH Absorption

Polypropylene nonwovens are prepared as in Example 1. The weight of additives based on the formulation is as in the table below. The nonwovens are cut into 4 square inch sections. The nonwovens are submerged in 167 mL of a 40% KOH solution at room temperature. After 5 minutes the samples are removed and allowed hang air dry for 1 minute. The samples are weighed to provide initial % KOH absorption (wet weight−dry weight/dry weight×100). The wet samples are again submerged in a fresh 40% KOH solution in covered beakers. The beakers are placed in a 70° C. oven. After 7 days the samples are removed and rinsed with deionized water. The samples are hang air dried for one day and weighed to provide % KOH absorption after 7 days at 70° C. Results are below.

| Unithox ® 420 (wt percent) | Atmer ® 502 (wt percent) | Initial Percent KOH absorption | Percent KOH Absorption after 7 Days at 70° C. |
|---|---|---|---|
| — | — | 618 | NA* |
| 1.5 | — | 881 | 900 |
| 3.0 | — | 777 | 822 |
| 1.5 | 1.5 | 824 | 1011 |
| 0.75 | 0.75 | 889 | 987 |

*The nonwoven polypropylene without additive has excess water beads, not absorption. It is seen that the hydrophilic nonwovens of the present invention perform well towards absorbing KOH solution even after annealing at 70° C. for 7 days. These results indicate potential of the present compositions in alkaline battery separator applications. Unithox ® 420 is equivalent to the present compound of formula (Ib).

What is claimed is:

1. A wettable polyolefin fiber or filament, comprising a melt blend which comprises
   (a) a polyolefin; and
   (b) at least one ethoxylated aliphatic alcohol of the formula

where x has an average value of 2.5.

2. A fiber or filament according to claim 1 in which the polyolefin is polypropylene or polyethylene.

3. A fiber or filament according to claim 1 wherein the compounds of component (b), in total, are present from about 0.1% to about 15% by weight, based on the weight of the polyolefin of component (a).

4. A fiber or filament according to claim 3 wherein the compounds of component (b), in total, are present from about 1% to about 7% by weight, based on the weight of the polyolefin of component (a).

5. A bi-component fiber comprising a polyolefin component, wherein the polyolefin component comprises a melt blend comprising components (a) and (b) according to claim 1.

6. A woven or nonwoven fabric comprising polyolefin fibers or filaments according to claim 1.

7. A woven or nonwoven fabric according to claim 6 wherein the polyolefin is polypropylene or polyethylene.

8. A woven or nonwoven fabric comprising bi-component fibers according to claim 5.

9. An article of manufacture comprising a woven or nonwoven fabric according to claim 6 selected from the group consisting of disposable diapers, training pants, feminine napkins, tampons, incontinence care products, wet and dry wipes, wound dressings, surgical capes, filter medial and battery separators.

10. A fiber or filament according to claim 1 in which the melt blend additionally comprises a different ethoxylated aliphatic alcohol.

11. A fiber or filament according to claim 1 in which the melt blend additionally comprises a 2 mole ethoxylated stearyl alcohol.

12. A fiber or filament according to claim 1 further comprising a stabilizer selected from the group consisting of hindered amine light stabilizers, phenolic antioxidants, phosphites or phosphonites, hydroxylamines, benzofuranones and hydroxyphenylbenzotriazole, hydroxybenzophenone or tris-aryl-s-triazine UV absorbers.

* * * * *